US010836864B2

(12) United States Patent
Fevre et al.

(10) Patent No.: US 10,836,864 B2
(45) Date of Patent: Nov. 17, 2020

(54) CHEMICAL COMPOSITIONS WITH ANTIMICROBIAL FUNCTIONALITY

(71) Applicants: International Business Machines Corporation, Armonk, NY (US); Agency for Science, Technology and Research, Connexis (SG)

(72) Inventors: Mareva B. Fevre, San Jose, CA (US); James L. Hedrick, Pleasanton, CA (US); Nathaniel H. Park, San Jose, CA (US); Victoria A. Piunova, Los Gatos, CA (US); Pang Kern Jeremy Tan, Singapore (SG); Chuan Yang, Hillington Green (SG); Yi Yan Yang, Singapore (SG)

(73) Assignees: INTERNATIONAL BUSINESS MACHINES CORPORATION, Armonk, NY (US); AGENCY FOR SCIENCE, TECHNOLOGY AND RESEARCH, Connexis (SG)

( * ) Notice: Subject to any disclaimer, the term of this patent is extended or adjusted under 35 U.S.C. 154(b) by 155 days.

(21) Appl. No.: 15/839,410

(22) Filed: Dec. 12, 2017

(65) Prior Publication Data

US 2019/0177479 A1 Jun. 13, 2019

(51) Int. Cl.
| | | |
|---|---|---|
| A61K 31/66 | (2006.01) | |
| A61K 31/787 | (2006.01) | |
| A61P 31/06 | (2006.01) | |
| C08G 73/02 | (2006.01) | |
| A61K 31/166 | (2006.01) | |
| C07C 13/47 | (2006.01) | |

(52) U.S. Cl.
CPC .......... *C08G 73/024* (2013.01); *A61K 31/166* (2013.01); *A61K 31/787* (2013.01); *A61P 31/06* (2018.01); *C07C 13/47* (2013.01); *C08G 73/0273* (2013.01); *C08G 73/0293* (2013.01)

(58) Field of Classification Search
CPC ............ C08G 73/0293; C08G 73/0273; C08G 73/024; A61K 31/787; A61K 31/166; A61P 31/06
See application file for complete search history.

(56) References Cited

U.S. PATENT DOCUMENTS

| | | | |
|---|---|---|---|
| 3,632,623 A | 1/1972 | Becke et al. | |
| 4,013,507 A | 3/1977 | Rembaum | |
| 4,032,596 A | 6/1977 | Uffner et al. | |
| 4,094,827 A | 6/1978 | McEntire | |
| 4,166,894 A | 9/1979 | Schaper | |
| 4,348,536 A | 9/1982 | Blahak et al. | |
| 4,698,391 A | 10/1987 | Yacobucci et al. | |
| 4,794,031 A | 12/1988 | Leir et al. | |
| 4,883,655 A | 11/1989 | Login et al. | |
| 5,419,897 A | 5/1995 | Drake et al. | |
| 5,681,862 A | 10/1997 | Hollis et al. | |
| 6,767,549 B2 | 7/2004 | Mandeville, III et al. | |
| 6,955,806 B2 | 10/2005 | Fitzpatrick et al. | |
| 8,541,477 B2 | 9/2013 | Alabdulrahman et al. | |
| 2006/0002889 A1 | 1/2006 | Fitzpatrick | |
| 2007/0025954 A1 | 2/2007 | Fitzpatrick et al. | |
| 2007/0106061 A1 | 5/2007 | Zollinger et al. | |
| 2012/0202979 A1 | 8/2012 | Wu | |
| 2013/0281515 A1 | 10/2013 | Coady et al. | |
| 2014/0275469 A1 | 9/2014 | Dhal et al. | |
| 2015/0038392 A1 | 2/2015 | Scheuing et al. | |
| 2016/0374335 A1 | 12/2016 | Chan et al. | |
| 2016/0375150 A1 | 12/2016 | Wu | |

FOREIGN PATENT DOCUMENTS

| | | |
|---|---|---|
| CN | 1192649 A | 9/1998 |
| CN | 1254334 A | 5/2000 |
| CN | 1518621 A | 8/2004 |
| CN | 101426507 A | 5/2009 |
| CN | 101646728 A | 2/2010 |
| CN | 105482105 A | 4/2016 |
| GB | 2 000 164 A | 1/1979 |
| JP | H03255139 A | 11/1991 |
| JP | 2004-224734 A | 8/2004 |
| JP | 2008214529 A | 9/2008 |
| WO | 97/02744 A1 | 1/1997 |
| WO | 98/54140 A1 | 12/1998 |
| WO | 02/080939 A2 | 10/2002 |

(Continued)

OTHER PUBLICATIONS

Liu, et al., Highly potent antimicrobial polyionenes with rapid killing kinetics, skin biocompatibility and in vivo bactericidal activity, Biomaterials, 2017, pp. 36-48, vol. 127.

Williams, et al., Recent advances in the synthesis and structure-property relationships of ammonium ionenes, Progress in Polymer Science, 2009, pp. 762-782, vol. 34.

Narita, et al., Effects of charge density and hydrophobicity of ionene polymer on cell binding and viability, Colloid Polym. Sci, 2000, pp. 884-887.

Mattheis, et al., Closing One of the Last Gaps in Polyionene Compositions: Alkyloxyethylammonium Ionenes as Fast-Acting Biocides, Macromolecular Bioscience, 2012, pp. 341-349, vol. 12.

Strassburg, et al., Nontoxic, Hydrophilic Cationic Polymers—Identified as Class of Antimicrobial Polymers, Macromolecular Bioscience, 2015, pp. 1710-1723, vol. 15.

(Continued)

*Primary Examiner* — Alma Pipic

(74) *Attorney, Agent, or Firm* — Amin, Turocy & Watson, LLP

(57) ABSTRACT

Techniques regarding killing of a pathogen with one or more ionene compositions having antimicrobial functionality are provided. For example, one or more embodiments can comprise a method, which can comprise contacting a *Mycobacterium tuberculosis* microbe with a chemical compound. The chemical compound can comprise an ionene unit. Also, the ionene unit can comprise a cation distributed along a molecular backbone. The ionene unit can have antimicrobial functionality. The method can further comprise electrostatically disrupting a membrane of the *Mycobacterium tuberculosis* microbe in response to the contacting.

9 Claims, 12 Drawing Sheets

(56) References Cited

FOREIGN PATENT DOCUMENTS

| WO | 02/099192 A2 | 12/2002 |
|---|---|---|
| WO | 2016/178634 A1 | 11/2016 |
| WO | 2016/186581 A1 | 11/2016 |
| WO | 2016/209732 A1 | 12/2016 |

OTHER PUBLICATIONS

Mayr, et al., Antimicrobial and Hemolytic Studies of a Series of Polycations Bearing Quaternary Ammonium Moieties: Structural and Topological Effects, International Journal of Molecular Sciences, 2017, 8 pages, vol. 18, No. 303.

Tamami, Synthesis and Characterization of Ammonium Ionenes Containing Hydrogen Bonding Functionalities, Dec. 6, 2012, 108 pages, Virginia Polytechnic Institute and State University.

Brown et al., The Structure Activity Relationship of Urea Derivatives as Anti-Tuberculosis Agents, Bioorg Med Chem. Sep. 15, 2011, pp. 5585-5595 vol. 19, No. 18.

Williams, Influence of Electrostatic Interactions and Hydrogen Bonding on the Thermal and Mechanical Properties of Step-Growth Polymers, Oct. 21, 2008, 375 pages, Virginia Polytechnic Institute and State University.

International Search Report and Written Opinion received for PCT Application Serial No. PCT/IB2018/059622, dated Mar. 28, 2019, 9 pages.

International Search Report and Written Opinion received for PCT Application Serial No. PCT/IB2018/059626, dated Apr. 15, 2019, 8 pages.

International Search Report and Written Opinion received for PCT Application Serial No. PCT/IB2018/059620, dated Mar. 27, 2019, 11 pages.

International Search Report and Written Opinion received for PCT Application Serial No. PCT/IB2018/059624 dated Apr. 17, 2019, 8 pages.

Non-Final Office Action received for U.S. Appl. No. 15/839,388 dated Jul. 10, 2019, 52 pages.

Murakami et al., "Syntheses of Macrocyclic Enzyme Models, Part 4. Preparation and Characterization of Cationic Octopus Azaparacyclophanes", Organic and Bio-Organic Chemistry, Journal of the Chemical Society, Perkin Transactions 1, Issue 11, Jan. 1, 1981, pp. 2800-2808.

Non-Final Office Action received for U.S. Appl. No. 15/839,199 dated Jun. 26, 2019, 66 pages.

Tiecco et al., "Biocidal and inhibitory activity screening of de novo synthesized surfactants against two eukaryotic and two prokaryotic microbial species", Science Direct, Colloids and Surfaces B: Biointerfaces, vol. 111, Nov. 1, 2013, 35 pages.

Non-Final Office Action received for U.S. Appl. No. 15/839,402 dated Jun. 26, 2019, 56 pages.

Odagi et al., "Origin of Stereocontrol in Guanidine-Bisurea Bifunctional Organocatalyst That Promotes α-Hydroxylation of Tetralone-Derived β-Ketoesters: Asymmetric Synthesis of β- and γ-Substituted Tetralone Derivatives via Organocatalytic Oxidative Kinetic Resolution", Journal of the American Chemical Society, Jan. 2015, pp. 1909-1915.

Magri et al., "Rethinking the old antiviral drug moroxydine: Discovery of novel analogues as anti-hepatitis C virus (HCV) agents", Bioorganic and Medicinal Chemistry Letters, vol. 25, No. 22, Nov. 2015, pp. 5372-5376.

Non-Final Office Action received for U.S. Appl. No. 15/839,415 dated Jul. 10, 2019, 29 pages.

International Search Report and Written Opinion received for PCT Application Serial No. PCT/IB2018/059621 dated Apr. 10, 2019, 8 pages.

Final Office Action received for U.S. Appl. No. 15/839,199 dated Sep. 26, 2019, 25 pages.

Non-Final Office Action received for U.S. Appl. No. 15/839,270 dated Sep. 16, 2019, 70 pages.

Non-Final Office Action received for U.S. Appl. No. 15/839,397 dated Sep. 17, 2019, 47 pages.

Wettig et al., "Thermodynamic and aggregation properties of aza- and imino-substituted gemini surfactants designed for gene delivery", Physical Chemistry Chemical Physics, vol. 9, 2007, pp. 871-877.

Notice of Allowance received for U.S. Appl. No. 15/839,402 dated Oct. 24, 2019, 113 pages.

Chahboune et al., "Application of liquid chromatography/electrospray ionization tandem mass spectrometry for the elucidation of hydroxyl radical oxidation of metsulfuron methyl and related sulfonylurea pesticide products: evidence for the triazine skeleton scission", Rapid Communications in Mass Spectrometry, vol. 29, Sep. 2015, pp. 1370-1380.

Rafqah et al., "Kinetics and mechanism of the degradation of the pesticde metsulfuron methyl induced by excitation of iron(III) aqua complexes in aqueous solutions: steady state and transient absorption spectroscopy studies", Photochem. Photobial. Sci., vol. 3, 2004, pp. 296-304.

Si et al., "Leaching and degradation of ethametsulfuron-methyl in soil", Cehmosphere, vol. 60, 2005, pp. 601-609.

Li-Feng et al., "Biodegradation of Ethametsulfuron-Methyl by *Pseudomonas* sp. SW4 Isolated from Contaminated Soil", Curr Microbial, vol. 55, 2007, pp. 420-426.

Final Office Action received for U.S. Appl. No. 15/839,415 dated Nov. 6, 2019, 29 pages.

Advisory Action received for U.S. Appl. No. 15/839,199, dated Nov. 19, 2019, 16 pages.

Non-Final Office Action received for U.S. Appl. No. 15/839,199 dated Dec. 26, 2019, 156 pages.

Haque et al., Synthesis, Characterization, and Crystal Structures of Bis-Imidazolium Salts and Respective Dinuclear Ag(I) N-Heterocyclic Carbene Complexes: In Vitro Anticancer Studies against "Human Colon Cancer" and "Breast Cancer", Hindawi Publishing Corporation Journal of Chemistry, 2013, 11 pages.

Wynne et al., "Synthesis and Development of a Multifunctional Self-Decontaminating Polyurethane Coating", Applied Materials and Interfaces, 2011, pp. 2005-2011.

Oi'Khovik et al., "Synthesis, Antimicrobial and Antifungal Activity of Double Quaternary Alnmonium Salts of Biphenyls", Russian Journal of General Chemistry, vol. 83, No. 2, 2013, pp. 329-335.

Jones et al., ortlo Substitution Rearrangement vs. β)—Elimination of Quaternary Ammonium Ion-Alcohols and Methyl Ether with Excess Sodium Amide[1], vol. 27 ,1962, pp. 806-814.

Menger et al., "Synthesis and Properties of Nine New Polyhydroxylated Surfactants", Langmuir, vol. 12, No. 6, 1996, pp. 1471-1473.

Final Office Action received for U.S. Appl. No. 15/839,397 dated Dec. 16, 2019, 31 pages.

Shen et al., "Synthesis of Highly Ordered Thermally Stable Cubic Mesostructured Zirconium Oxophosphate Templated by Tri-Headgroup Quaternary Ammonium Surfactants", Chem. Mater, vol. 15, No. 21, 2003, pp. 1046-4051.

Wang et al., "Transfection and structural properties of phytanyl substituted gemini surfactant-based vectors for gene delivery", Phys. Chem. Chem. Phys., 2013, vol. 15, pp. 20510-20516.

Final Office Action received for U.S. Appl. No. 15/839,388 dated Dec. 5, 2019, 43 pages.

Office Action for U.S. Appl. No. 16/829,370, dated Sep. 8, 2020, 50 pages.

Office Action for U.S. Appl. No. 16/744,868, dated Aug. 6, 2020, 56 pages.

200 ⬅
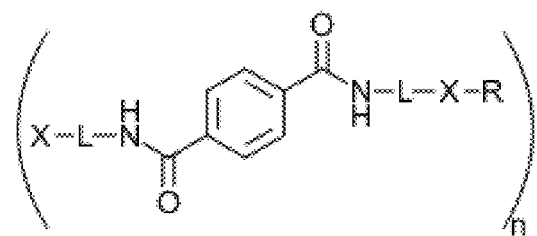
202 ⬅
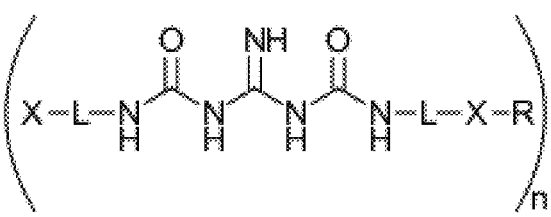
FIG. 2

602 — CONTACTING A MYCOBACTERIUM TUBERCULOSIS MICROBE WITH A CHEMICAL COMPOUND, THE CHEMICAL COMPOUND COMPRISING AN IONENE UNIT, AND THE IONENE UNIT COMPRISING A CATION DISTRIBUTED ALONG A MOLECULAR BACKBONE, WHEREIN THE IONENE UNIT HAS ANTIMICROBIAL FUNCTIONALITY

604 — ELECTROSTATICALLY DISRUPTING A MEMBRANE OF THE MYCOBACTERIUM TUBERCULOSIS MICROBE IN RESPONSE TO THE CONTACTING

702 — CONTACTING A MYCOBACTERIUM AVIUM COMPLEX MICROBE WITH A CHEMICAL COMPOUND, THE CHEMICAL COMPOUND COMPRISING AN IONENE UNIT, AND THE IONENE UNIT COMPRISING A CATION DISTRIBUTED ALONG A MOLECULAR BACKBONE, WHEREIN THE IONENE UNIT HAS ANTIMICROBIAL FUNCTIONALITY

704 — ELECTROSTATICALLY DISRUPTING A MEMBRANE OF THE MYCOBACTERIUM AVIUM COMPLEX MICROBE IN RESPONSE TO THE CONTACTING

```
┌─────────────────────────────────────────────────────────┐
│ CONTACTING A PATHOGEN WITH A CHEMICAL COMPOUND, THE     │
│ CHEMICAL COMPOUND COMPRISING AN IONENE UNIT, THE        │──802
│ IONENE UNIT COMPRISING A CATION DISTRIBUTED ALONG A     │
│ MOLECULAR BACKBONE, AND THE MOLECULAR BACKBONE          │
│ COMPRISING A BIS(UREA)GUANIDINIUM STRUCTURE, WHEREIN    │
│ THE IONENE UNIT HAS ANTIMICROBIAL FUNCTIONALITY         │
└─────────────────────────────────────────────────────────┘
                            │
                            ▼
┌─────────────────────────────────────────────────────────┐
│ ELECTROSTATICALLY DISRUPTING A MEMBRANE OF THE          │──804
│ PATHOGEN IN RESPONSE TO THE CONTACTING                  │
└─────────────────────────────────────────────────────────┘
```

```
┌─────────────────────────────────────────────────────────┐
│ CONTACTING A PATHOGEN WITH A CHEMICAL COMPOUND, THE     │
│ CHEMICAL COMPOUND COMPRISING AN IONENE UNIT, THE        │── 902
│ IONENE UNIT COMPRISING A CATION DISTRIBUTED ALONG A     │
│ MOLECULAR BACKBONE, AND THE MOLECULAR BACKBONE          │
│ COMPRISING A TEREPHTHALAMIDE STRUCTURE, WHEREIN THE     │
│ IONENE UNIT HAS ANTIMICROBIAL FUNCTIONALITY             │
└─────────────────────────────────────────────────────────┘
                             │
                             ▼
┌─────────────────────────────────────────────────────────┐
│ ELECTROSTATICALLY DISRUPTING A MEMBRANE OF THE          │── 904
│ PATHOGEN IN RESPONSE TO THE CONTACTING                  │
└─────────────────────────────────────────────────────────┘
```

TARGETING A PATHOGEN WITH A CHEMICAL COMPOUND THROUGH ELECTROSTATIC INTERACTION BETWEEN THE CHEMICAL COMPOUND AND A MEMBRANE OF THE PATHOGEN, THE CHEMICAL COMPOUND COMPRISING AN IONENE UNIT, THE IONENE UNIT COMPRISING A CATION DISTRIBUTED ALONG A MOLECULAR BACKBONE, AND THE IONENE UNIT COMPRISING A HYDROPHOBIC FUNCTIONAL GROUP COVALENTLY BONDED TO THE MOLECULAR BACKBONE — 1002

DESTABILIZING THE MEMBRANE OF THE PATHOGEN THROUGH INTEGRATION OF THE HYDROPHOBIC FUNCTIONAL GROUP INTO THE MEMBRANE OF THE PATHOGEN — 1004

| Ionene Composition | SA (µg/mL) | EC (µg/mL) | PA (µg/mL) | CA (µg/mL) | Mtb 3360 (µg/mL) | Mtb 3361 (µg/mL) |
|---|---|---|---|---|---|---|
| First Ionene Composition 300 | 3.9 | 7.8 | 7.8 | 7.8 | 8 | 16 |
| Second Ionene Composition 402 | 8 | 8 | 8 | 16 | 8 | 8 |
| Third Ionene Composition 404 | 4 | 8 | 8 | 16 | 8 | 8 |
| Fourth Ionene Composition 406 | 8 | 16 | 31 | 8 | 8 | 8 |
| Fifth Ionene Composition 408 | 250 | >1000 | 500 | 1000 | 16 | 16 |
| Sixth Ionene Composition 410 | 4 | 8 | 4 | 8 | 8 | 8 |
| Seventh Ionene Composition 412 | 8 | 8 | 8 | 8 | 16 | 16 |
| Eighth Ionene Composition 414 | N/A | N/A | N/A | N/A | 16 | 16 |
| Ninth Ionene Composition 502 | 31 | 31 | 63 | 2 | 8 | 16 |
| Tenth Ionene Composition 504 | 4-8 | 8-16 | 16 | 8-16 | 2 | 2-4 |
| Eleventh Ionene Composition 506 | 63 | 31 | >500 | 31 | 2 | 4 |

FIG. 12A

| Ionene Composition | Mycobacterium avium complex (µg/mL) | Mycobacterium abscessus 4064 (µg/mL) |
|---|---|---|
| Fifth Ionene Composition 408 | 8 | 128 |
| Eighth Ionene Composition 414 | 16 | 32 |
| Ninth Ionene Composition 502 | N/A | 16 |
| Tenth Ionene Composition 504 | N/A | 64 |

FIG. 12B

CHEMICAL COMPOSITIONS WITH ANTIMICROBIAL FUNCTIONALITY

BACKGROUND

The subject disclosure relates to one or more ionene compositions with antimicrobial functionality, and more specifically, to one or more ionene compositions capable of killing and/or preventing growth of a pathogen.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, methods and/or compositions regarding ionene compositions with antimicrobial functionality are described.

According to an embodiment, a method is provided. The method can comprise contacting a *Mycobacterium tuberculosis* microbe with a chemical compound. The chemical compound can comprise an ionene unit. Also, the ionene unit can comprise a cation distributed along a molecular backbone. The ionene unit can have antimicrobial functionality. The method can further comprise electrostatically disrupting a membrane of the *Mycobacterium tuberculosis* microbe in response to the contacting.

According to another embodiment, a method is provided. The method can comprise contacting a *Mycobacterium avium* complex microbe with a chemical compound. The chemical compound can comprise an ionene unit. Also, the ionene unit can comprise a cation distributed along a molecular backbone. The ionene unit can have antimicrobial functionality. The method can further comprise electrostatically disrupting a membrane of the *Mycobacterium avium* complex microbe in response to the contacting.

According to another embodiment, a method is provided. The method can comprise contacting a pathogen with a chemical compound. The chemical compound can comprise an ionene unit. The ionene unit can comprise a cation distributed along a molecular backbone. Additionally, the molecular backbone can comprise a bis(urea)guanidinium structure, and the ionene unit can have antimicrobial functionality. The method can further comprise electrostatically disrupting a membrane of the pathogen in response to the contacting.

According to another embodiment, a method is provided. The method can comprise contacting a pathogen with a chemical compound. The chemical compound can comprise an ionene unit. Also, the ionene unit can comprise a cation distributed along a molecular backbone. The molecular backbone can comprise a terephthalamide structure, and the ionene unit can have antimicrobial functionality. The method can further comprise electrostatically disrupting a membrane of the pathogen in response to the contacting.

According to another embodiment, a method is provided. The method can comprise targeting a pathogen with a chemical compound through electrostatic interaction between the chemical compound and a membrane of the pathogen. The chemical compound can comprise an ionene unit. The ionene unit can comprise a cation distributed along a molecular backbone. Additionally, the ionene unit can comprise a hydrophobic functional group covalently bonded to the molecular backbone. The method can further comprise destabilizing the membrane of the pathogen through integration of the hydrophobic functional group into the membrane of the pathogen.

BRIEF DESCRIPTION OF THE DRAWINGS

FIG. 2 illustrates a diagram of example, non-limiting chemical formulas that can characterize one or more ionene units in accordance with one or more embodiments described herein.

FIG. 6 illustrates a flow diagram of an example, non-limiting method that can facilitate killing of a *Mycobacterium tuberculosis* microbe in accordance with one or more embodiments described herein.

FIG. 7 illustrates a flow diagram of an example, non-limiting method that can facilitate killing of a *Mycobacterium avium* complex microbe in accordance with one or more embodiments described herein.

FIG. 8 illustrates a flow diagram of an example, non-limiting method that can facilitate killing of a pathogen in accordance with one or more embodiments described herein.

FIG. 9 illustrates a flow diagram of an example, non-limiting method that can facilitate killing of a pathogen in accordance with one or more embodiments described herein.

FIG. 10 illustrates a flow diagram of an example, non-limiting method that can facilitate killing of a pathogen in accordance with one or more embodiments described herein.

FIG. 12A illustrates a diagram of an example, non-limiting chart that can depict antimicrobial efficacy of one or more ionene compositions in accordance with one or more embodiments described herein.

FIG. 12B illustrates a diagram of an example, non-limiting chart that can depict antimicrobial efficacy of one or more ionene compositions in accordance with one or more embodiments described herein.

DETAILED DESCRIPTION

Figure 1A:
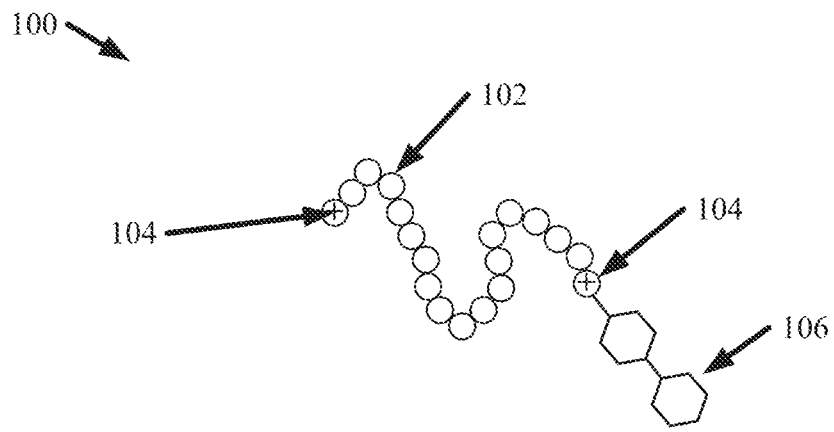
FIG. 1A illustrates a diagram of an example, non-limiting ionene unit in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

The discovery and refinement of antibiotics was one of the crowning achievements in the 20th century that revolutionized healthcare treatment. For example, antibiotics such as penicillin, ciprofloxacin and, doxycycline can achieve microbial selectivity through targeting and disruption of a specific prokaryotic metabolism, while concurrently, remaining benign toward eukaryotic cells to afford high selectivity. If properly dosed, they could eradicate infection. Unfortunately, this therapeutic specificity of antibiotics also leads to their undoing as under-dosing (incomplete kill) allows for minor mutative changes that mitigate the effect of the antibiotic leading to resistance development. Consequently, nosocomial infections, caused by medication-resistant microbes such as methicillin-resistant *Staphylococcus aureus* (MRSA), multi-medication-resistant *Pseudomonas aeruginosa* and vancomycin-resistant Enterococci (VRE) have become more prevalent. An added complexity is the pervasive use of antimicrobial agents in self-care products, sanitizers and hospital cleaners etc, including anilide, bis-phenols, biguanides and quaternary ammonium compounds, where a major concern is the development of cross- and co-resistance with clinically used antibiotics, especially in a hospital setting. Another unfortunate feature with triclosan, for example, is its cumulative and persistent effects in the skin. Moreover, biofilms have been associated with numerous nosocomial infections and implant failure, yet the eradication of biofilms is an unmet challenge to this date. Since antibiotics are not able to penetrate through extracellular polymeric substance that encapsulates bacteria in the biofilm, further complexities exist that lead to the development of medication resistance.

Current antibiotic therapies are inefficient to treat biofilm protected and intracellular infections such as *Mycobacterium tuberculosis* (TB) and related strains, allowing bacteria to establish chronic medication resistant infections. The Gates Foundation estimates that 8.6 million new TB cases are reported each year resulting in 1.3 million deaths worldwide. The World Health Organization (WHO) estimates approximately 9 to 10 million new TB cases per year. Pulmonary non-tuberculosis mycobacteria (NTM) cases, including *Mycobacterium avium* complex (MAC), are estimated by some experts to be at least ten times more common than TB in the U.S., with at least 150,000 new cases per year. Given the reduction of effective treatment options for TB and MAC, and diminished antibiotic discovery and development pipeline, a new therapeutic development paradigm is needed for perpetual treatment of increasingly resistant TB and MAC infections.

TB and other mycobacteria strains including MAC can be extremely difficult to eradicate compared to other types of bacteria due to their ability to encapsulate bacterial colonies with extracellular biofilm secretions to block existing antibiotic activity. However, chemical compounds having a cationic charge can provide electrostatic disruption of the bacterial membrane interaction. Furthermore, cationic polymers can be readily made amphiphilic with addition of hydrophobic regions permitting both membrane association and integration/lysis. The amphiphilic balance has shown to play an important effect not only in the antimicrobial properties but also in the hemolytic activity. Many of these antimicrobial chemical compounds can show relatively low selectivity as defined by the relative toxicity to mammalian cells or hemolysis relative to pathogens.

Various embodiments described herein can regard chemical compounds and/or methods that can target mycolic acid, a cell wall component of the *Mycobacterium tuberculosis* (Mtb) bacilli, using a mechanism of action that can prevent resistance development and can avoid nonspecific toxicity. For example, one or more embodiments described herein can comprise small molecular compounds and macromolecular chemical compounds, which can have bis(urea) guanidinium functionalities. The bis(urea)guanidine structure can allow for a unique combination of hydrogen-bonding capabilities with strong association constants with the mycolic acid. Collectively, ionic interactions associated with the cationic charges on the chemical compounds together with the hydrogen bonding associated with the bis(urea)guanidine structures can provide a cooperative but orthogonal association with Mtb through the mycolic acid that can amplify the targeting, selectivity and potency towards Mtb. Further, said physical interactions can prevent resistance development. Additionally, one or more embodiments described herein (e.g., methods of killing a pathogen comprising one or more chemical compounds having a bis(urea)guanidinium structure) can exhibit negligible toxicity against L929 mouse fibroblast cell line, and cell viability can be more than 85% after 48-h incubation with the compound at 250 micrograms per milliliter (μg/mL), which is well above its minimum inhibitory concentration (MIC) (e.g., 2-4 μg/mL).

As used herein, the term "ionene" can refer to a polymer unit, a copolymer unit, and/or a monomer unit that can comprise a nitrogen cation and/or a phosphorus cation distributed along, and/or located within, a molecular backbone, thereby providing a positive charge. Example nitrogen cations include, but are not limited to: quaternary ammonium cations, protonated secondary amine cations, protonated tertiary amine cations, and/or imidazolium cations. Example, phosphorus cations include, but are not limited to: quaternary phosphonium cations, protonated secondary phosphine cations, and protonated tertiary phosphine cations. As used herein, the term "molecular backbone" can refer to a central chain of covalently bonded atoms that form the primary structure of a molecule. In various embodiments described herein, side chains can be formed by bonding one or more functional groups to a molecular backbone. As used herein, the term "polyionene" can refer to a polymer that can comprise a plurality of ionenes. For example, a polyionene can comprise a repeating ionene.

FIG. 1A illustrates a diagram of an example, non-limiting ionene unit 100 in accordance with one or more embodiments described herein. The ionene unit 100 can comprise a molecular backbone 102, one or more cations 104, and/or one or more hydrophobic functional groups 106. In various embodiments, an ionene and/or a polyionene described herein can comprise the ionene unit 100. For example, a polyionene described herein can comprise a plurality of ionenes bonded together, wherein the bonded ionenes can have a composition exemplified by ionene unit 100.

Figure 1B:
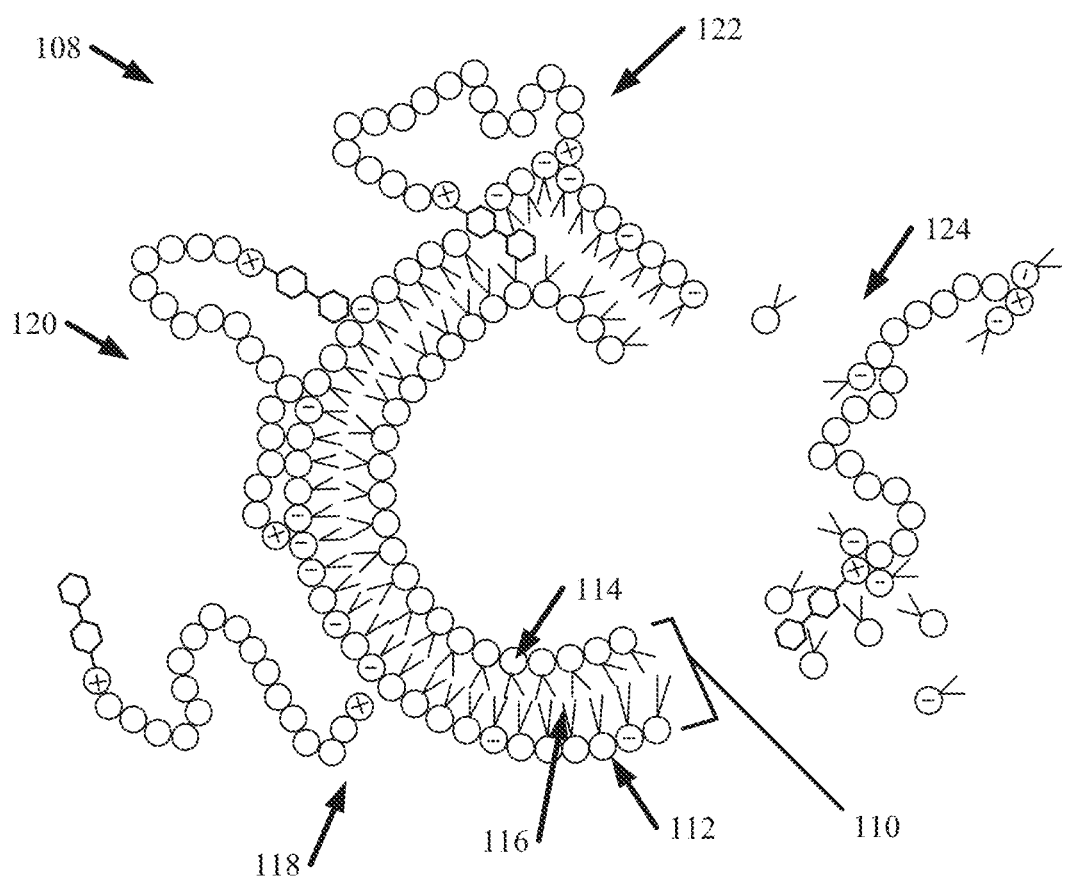
FIG. 1B illustrates a diagram of an example, non-limiting lysis process that can be performed by one or more ionene units in accordance with one or more embodiments described herein.

The molecular backbone 102 can comprise a plurality of covalently bonded atoms (illustrated as circles in FIGS. 1A and 1B). The atoms can be bonded in any desirable formation, including, but not limited to: chain formations, ring formations, and/or a combination thereof. The molecular backbone 102 can comprise one or more chemical structures including, but not limited to: alkyl structures, aryl structures, alkane structures, aldehyde structures, ester structures, carboxyl structures, carbonyl structures, amine structures, amide structures, phosphide structures, phosphine structures, a combination thereof, and/or the like. One of ordinary skill in the art will recognize that the number of atoms that can comprise the molecular backbone can vary depending of the desired function of the ionene unit 100. For example, while nineteen atoms are illustrated in FIG. 1A, a molecular backbone 102 that can comprise dozens, hundreds, and/or thousands of atoms is also envisaged.

Located within the molecular backbone 102 are one or more cations 104. As described above, the one or more cations 104 can comprise nitrogen cations and/or phosphorous cations. The cations 104 can be distributed along the molecular backbone 102, covalently bonded to other atoms within the molecular backbone 102. In various embodiments, the one or more cations 104 can comprise at least a portion of the molecular backbone 102. One of ordinary skill in the art will recognize that the number of a cations 104 that can comprise the ionene unit 100 can vary depending of the desired function of the ionene unit 100. For example, while two cations 104 are illustrated in FIG. 1A, an ionene unit 100 that can comprise dozens, hundreds, and/or thousands of cations 104 is also envisaged. Further, while FIG. 1A illustrates a plurality of cations 104 evenly spaced apart, other configurations wherein the cations 104 are not evenly spaced apart are also envisaged. Also, the one or more cations 104 can be located at respective ends of the molecular backbone 102 and/or at intermediate portions of the molecular backbone 102, between two or more ends of the molecular backbone 102. The one or more cations 104 can provide a positive charge to one or more locations of the ionene unit 100.

The one or more hydrophobic functional groups 106 can be bonded to the molecular backbone 102 to form a side chain. The one or more of the hydrophobic functional groups 106 can be attached to the molecular backbone 102 via bonding with a cation 104. Additionally, one or more hydrophobic functional groups 106 can be bonded to an electrically neutral atom of the molecular backbone 102. The ionene unit 100 can comprise one or more hydrophobic functional groups 106 bonded to: one or more ends of the molecular backbone 102, all ends of the molecular backbone 102, an intermediate portion (e.g., a portion between two ends) of the molecular backbone 102, and/or a combination thereof.

While a biphenyl group is illustrated in FIG. 1A as the hydrophobic functional group 106, other functional groups that are hydrophobic are also envisaged. Example, hydrophobic functional groups 106 can include, but are not limited to: alkyl structures, aryl structures, alkane structures, aldehyde structures, ester structures, carboxyl structures, carbonyl structures, carbonate structures, alcohol structures, a combination thereof, and/or the like. In various embodiments, the one or more hydrophobic functional groups 106 can comprise the same structure. In other embodiments, one or more of the hydrophobic functional groups 106 can comprise a first structure and one or more other hydrophobic functional groups 106 can comprise another structure.

FIG. 1B illustrates a diagram of an example, non-limiting lysis process 108 that can be facilitated by the ionene unit 100 in accordance with one or more embodiments described herein. Repetitive description of like elements employed in other embodiments described herein is omitted for sake of brevity. The lysis process 108 can comprise a plurality of stages, which can collectively comprise an attack mechanism that can be performed by the ionene unit 100 against a pathogen cell. Example pathogen cells can include, but are not limited to: Gram-positive bacteria cells, Gram-negative bacteria cells, fungi cells, yeast cells, *Mycobacterium tuberculosis* microbes, *Mycobacterium avium* complex microbes, and/or *Mycobacterium abscessus* microbes.

The target pathogen cell can comprise a membrane having a phospholipid bilayer 110. In various embodiments, the membrane can be an extracellular matrix. The phospholipid bilayer 110 can comprise a plurality of membrane molecules 112 covalently bonded together, and the membrane molecules 112 can comprise a hydrophilic head 114 and one or more hydrophobic tails 116. Further, one or more of the plurality of membrane molecules 112 can be negatively charged (as illustrated in FIG. 1B with a "−" symbol).

At 118, electrostatic interaction can occur between the positively charged cations 104 of the ionene unit 100 and one or more negatively charged membrane molecules 112. For example, the negative charge of one or more membrane molecules 112 can attract the ionene unit 100 towards the membrane (e.g., the phospholipid bilayer 110). Also, the electrostatic interaction can electrostatically disrupt the integrity of the membrane (e.g., phospholipid bilayer 110). Once the ionene unit 100 has been attracted to the membrane (e.g., phospholipid bilayer 110), hydrophobic membrane integration can occur at 120. For example, at 120 one or more hydrophobic functional groups 106 of the ionene unit 100 can begin to integrate themselves into the phospholipid bilayer 110. While the positively charged portions of the ionene unit 100 are attracted, and electrostatically disrupting, one or more negatively charged membrane molecules 112 (e.g., one or more hydrophilic heads 114), the one or more hydrophobic functional groups 106 can insert themselves between the hydrophilic heads 114 to enter a hydrophobic region created by the plurality of hydrophobic tails 116.

As a result of the mechanisms occurring at 118 and/or 120, destabilization of the membrane (e.g., the phospholipid bilayer 110) can occur at 122. For example, the one or more hydrophobic functional groups 106 can serve to cleave one or more negatively charged membrane molecules 112 from adjacent membrane molecules 112, and the positively charged ionene unit 100 can move the cleaved membrane segment (e.g., that can comprise one or more negatively charged membrane molecules 112 and/or one or more neutral membrane molecules 112 constituting a layer of the phospholipid bilayer 110) away from adjacent segments of the membrane (e.g., adjacent segments of the phospholipid bilayer 110). As cleaved segments of the membrane (e.g., the phospholipid bilayer 110) are pulled away, they can fully detach from other membrane molecules 112 at 124, thereby forming gaps in the membrane (e.g., the phospholipid bilayer 110). The formed gaps can contribute to lysis of the subject pathogen cell. In various embodiments, a plurality of ionene units 100 can perform the lysis process 108 on a cell simultaneously. Furthermore, the ionene units 100 participating in a lysis process 108 need not perform the same stages of the attack mechanism at the same time.

FIG. 2 illustrates a diagram of example, non-limiting chemical formulas that can characterize one or more ionene compositions in accordance with one or more embodiments described herein. Repetitive description of like elements employed in other embodiments described herein is omitted for sake of brevity. The first chemical formula 200 can characterize one or more ionene units 100 comprising a molecular backbone 102 with one or more terephthalamide structures. The second chemical formula 202 can characterize one or more ionene units with a molecular backbone 102 comprising one or more bis(urea)guanidinium structures. The chemical formulas depicted in FIG. 2 (e.g., the first chemical formula 200 and/or the second chemical formula 202) can comprise monomers and/or polymers (e.g., homopolymers, alternating copolymers, and/or random copolymers). In addition, the one or more ionene units 100 that can be characterized by the first chemical formula 200 can be bonded to one or more other ionene units 100 that can be characterized by the second chemical formula 200 to form one or more chemical compounds (e.g., ionenes, polyionones, monomers, and/or polymers).

As shown in FIG. 2, an ionene unit 100 characterized by the first chemical formula 200 and/or the second chemical formula 202 can comprise a degradable molecular backbone 102. In one or more embodiments, an ionene unit 100 characterized by the first chemical formula 200 can be derived from polyethylene terephthalate ("PET"), wherein the one or more terephthalamide structures can be derived from the PET. However, one or more embodiments of the first chemical formula 200 can comprise one or more terephthalamide structures derived from one or more molecules other than PET. In various embodiments, an ionene unit 100 characterized by the second chemical formula 202 can be derived from 1,3-bis(butoxycarbonyl)guanidine, wherein the one or more guanidinium groups can be derived from the 1,3-bis(butoxycarbonyl)guanidine. However, one or more embodiments of the second chemical formula 202 can comprise one or more bis(urea)guanidinium structures derived from one or more molecules other than 1,3-bis(butoxycarbonyl)guanidine.

The "X" in FIG. 2 can represent the one or more cations 104. For example, "X" can represent one or more cations 104 selected from a group that can include, but is not limited to: one or more nitrogen cations, one or more phosphorus cations, and/or a combination thereof. For instance, "X" can represent one or more nitrogen cations selected from a group that can include, but is not limited to: one or more protonated secondary amine cations, one or more protonated tertiary amine cations, one or more quaternary ammonium cations, one or more imidazolium cations, and/or a combination thereof. In another instance, "X" can represent one or more phosphorus cations selected from a group that can include, but is not limited to: one or more protonated secondary phosphine cations, one or more protonated tertiary phosphine cations, one or more quaternary phosphonium cations, and/or a combination thereof.

The one or more cations 104 (e.g., represented by "X" in the first chemical formula 200 and/or the second chemical formula 202) can be covalently bonded to one or more linkage groups to form, at least a portion, of the degradable molecular backbone 102. The one or more linkage groups can link the one or more cations 104 to one or more terephthalamide structures (e.g., as characterized by the first chemical formula 200) and/or one or more bis(urea)guanidinium structures (e.g., as characterized by the second chemical formula 202), thereby comprising the molecular backbone 102. The "L" in FIG. 2 can represent the one or more linkage groups. The one or more linkage groups can comprise any structure in compliance with the various features of the molecular backbone 102 described herein. For example, the one or more linkage groups can have any desirable formation, including, but not limited to: chain formations, ring formations, and/or a combination thereof. The one or more linkage groups can comprise one or more chemical structures including, but not limited to: alkyl structures, aryl structures, alkenyl structures, aldehyde structures, ester structures, carboxyl structures, carbonyl structures, a combination thereof, and/or the like. For instance, "L" can represent one or more linkage groups that can comprise an alkyl chain having greater than or equal to two carbon atoms and less than or equal to 15 carbon atoms.

As shown in FIG. 2, in various embodiments, one or more ionene units 100 characterized by the first chemical formula 200 and/or the second chemical formula 202 can comprise cations 104 (e.g., represented by "X") at a plurality of locations along the molecular backbone 102. For example, cations 104 can be located at either end of the molecular backbone 102 (e.g., as illustrated in FIG. 2). However, in one or more embodiments of the first chemical formula 200 and/or the second chemical formula 202, the molecular backbone 102 can comprise less or more cations 104 than the two illustrated in FIG. 2.

Further, the "R" shown in FIG. 2 can represent the one or more hydrophobic functional groups 106 in accordance with the various embodiments described herein. For example, the one or more hydrophobic functional groups 106 can comprise one or more alkyl groups and/or one or more aryl groups. For instance, the hydrophobic functional group 106 can be derived from one or more dialkyl halides. Example dialkyl halides can include, but are not are not limited to: p-xylylene dichloride, 4,4'-bis(chloromethyl)biphenyl; 1,4-bis(bromomethyl)benzene; 4,4'-bis(bromomethyl)biphenyl; 1,4-bis(iodomethyl)benzene; 1,6-dibromohexane; 1,8-dibromooctane; 1,12-dibromododecane; 1,6-dichlorohexane; 1,8-dichlorooctane; a combination thereof; and/or the like. The one or more hydrophobic functional groups 106 (e.g., represented by "R" in FIG. 2) can be covalently bonded to one or more of the cations 104 (e.g., represented by "X" in FIG. 2) and/or the molecular backbone 102, which can comprise the one or more cations 104 (e.g., represented by "X" in FIG. 2), one or more linkage groups (e.g., represented by "L" in FIG. 2), and/or one or more bis(urea)guanidinium structures and/or terephthalamide structures.

In one or more embodiments, one or more ionene units 100 characterized by the first chemical formula 200 can also comprise one or more hydrophilic functional groups. The one or more hydrophilic functional groups can: increase degradability of the one or more ionene units 100, impart carbohydrate mimetic functionality to the one or more ionene units 100, and/or increase mobility (e.g., intracellular mobility) of the one or more ionene units 100. For example, the one or more hydrophilic functional groups can be derived from a polyol and have one or more hydroxyl functional groups. In another example, the one or more hydrophilic functional groups can be derived from a block polymer, can be water-soluble, can be bioinert, and/or can comprise one or more ether groups.

Additionally, one or more ionene units 100 characterized by the second chemical formula 202 can have supramolecular functionality. For example, the one or more bis(urea) guanidinium structures can facilitate supramolecular assembly of the one or more ionene units 100 to form a supramolecule.

Moreover, an ionene and/or polyionene characterized by the first chemical formula 200 and/or the second chemical formula 202 can comprise a single ionene unit 100 or a repeating ionene unit 100. For example, the "n" shown in FIG. 2 can represent a first integer greater than or equal to one and less than or equal to one thousand.

Figure 3:
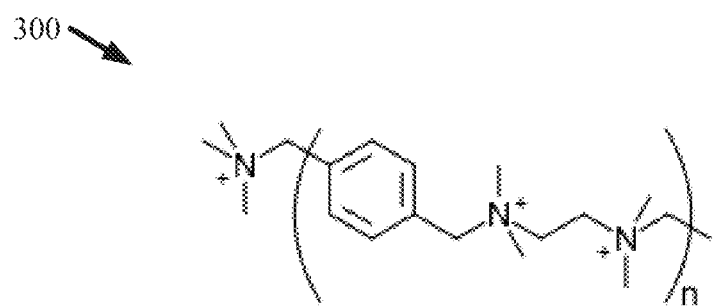
FIG. 3 illustrates a diagram of an example, non-limiting ionene composition that can be utilized in accordance with one or more embodiments described herein.

FIG. 3 illustrates an example, non-limiting first ionene composition 302 comprising an ionene unit 100 in accordance with one or more embodiments described herein. Repetitive description of like elements employed in other embodiments described herein is omitted for sake of brevity. For example, the first ionene composition 302 can be in accordance with the various features described herein regarding FIG. 1A-1B. The one or more cations 104 comprising the first ionene composition 302 can be quaternary ammonium cations. Additionally, the one or more hydrophobic functional groups 106 comprising the first ionene composition 302 can be an aromatic ring along the first ionene composition's 302 molecular backbone 102. Moreover, the "n" shown in FIG. 3 can represent an integer greater than or equal to one and less than or equal to one thousand.

Figure 4:
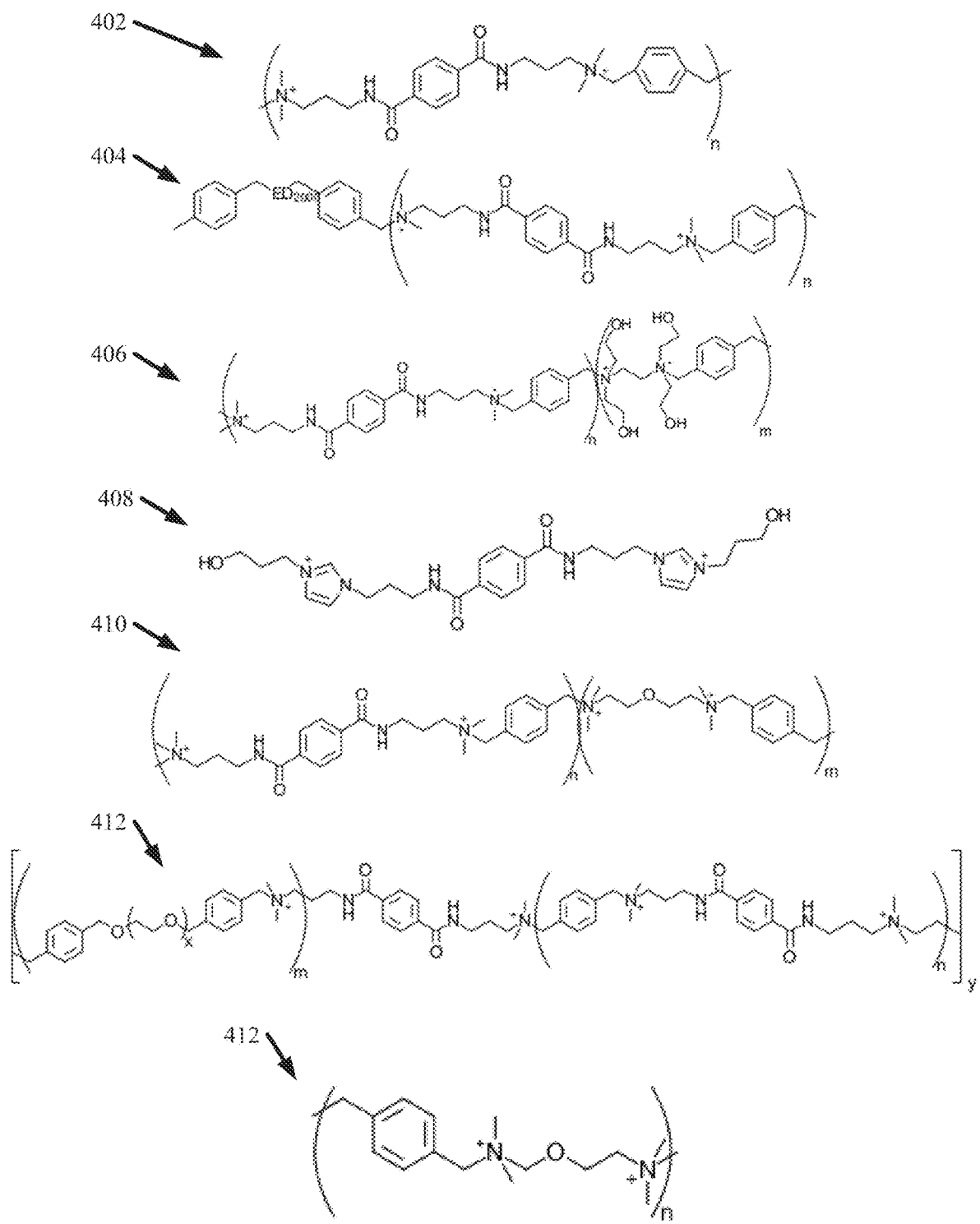
FIG. 4 illustrates a diagram of example, non-limiting ionene compositions that can be utilized in accordance with one or more embodiments described herein.

FIG. 4 illustrates example, non-limiting ionene compositions that can be characterized by the first chemical formula 200 in accordance with one or more embodiments described herein. Repetitive description of like elements employed in other embodiments described herein is omitted for sake of brevity. The "n" shown in FIG. 4 can represent an integer greater than or equal to one and less than or equal to one thousand. The "m" shown in FIG. 4 can represent another integer greater than or equal to one and less than or equal to one thousand. The "x" shown in FIG. 4 can represent another integer greater than or equal to one and less than or equal to one thousand. The "y" shown in FIG. 4 can represent another integer greater than or equal to one and less than or equal to one thousand. The ionene compositions depicted in FIG. 4 can comprise monomers and/or polymers (e.g., homopolymers, alternating copolymers, and/or random copolymers).

The second ionene composition 402 (e.g., comprising an ionene unit 100 that can be characterized by the first chemical formula 200) can comprise a degradable molecular backbone 102 having one or more terephthalamide structures. The one or more cations 104 of the second composition 402 can be quaternary ammonium cations. Further, the one or more hydrophobic functional groups 106 can comprise one or more aromatic rings bonded to one or more of the cations 104 (e.g., one or more quaternary ammonium cations).

The third ionene composition 404 (e.g., comprising an ionene unit 100 that can be characterized by the first chemical formula 200) can comprise a degradable molecular backbone 102 having one or more terephthalamide structures. The one or more cations 104 of the third composition 404 can be quaternary ammonium cations. Further, the one or more hydrophobic functional groups 106 can comprise one or more aromatic rings bonded to one or more of the cations 104 (e.g., one or more quaternary ammonium cations). Moreover, the third ionene composition 404 can comprise one or more hydrophilic functional groups. The one or more hydrophilic functional groups can be: derived from a block polymer, water-soluble, and/or bioinert. The one or more hydrophilic functional groups can be bonded to one or more cations 104 (e.g., quaternary ammonium cations). For example, the one or more hydrophilic functional groups can comprise a poly(propylene glycol)-block-poly(ethylene glycol)-block-poly(propylene glycol) bis(2-aminopropyl ether) (ED) structure having a molecular weight greater than or equal to 1900 grams per mole (g/mol) and less than or equal to 2200 g/mol ($ED_{2000}$).

The fourth ionene composition 406 (e.g., comprising an ionene unit 100 that can be characterized by the first chemical formula 200) can comprise a degradable molecular backbone 102 having one or more terephthalamide structures. The one or more cations 104 of the fourth composition 406 can be quaternary ammonium cations. Further, the one or more hydrophobic functional groups 106 can comprise one or more aromatic rings bonded to one or more of the cations 104 (e.g., one or more quaternary ammonium cations). Moreover, the fourth ionene composition 406 can comprise one or more hydrophilic functional groups. The one or more hydrophilic functional groups can be derived from a polyol, can comprise one or more hydroxyl groups, and/or can exhibit carbohydrate mimetic functionality. Also, the one or more hydrophilic functional groups can be bonded to the one or more hydrophobic functional groups 106. In addition, the one or more hydrophilic functional groups can comprise additional cations 104 (e.g., quaternary ammonium cations).

The fifth ionene composition 408 (e.g., comprising an ionene unit 100 that can be characterized by the first chemical formula 200) can comprise a degradable molecular backbone 102 having one or more terephthalamide structures. The one or more cations 104 of the fifth composition 408 can be imidazolium cations. Further, the one or more hydrophobic functional groups 106 can comprise one or more alkyl chains bonded to one or more of the cations 104 (e.g., one or more imidazolium cations).

The sixth ionene composition 410 (e.g., comprising an ionene unit 100 that can be characterized by the first chemical formula 200) can comprise a degradable molecular backbone 102 having one or more terephthalamide structures. The one or more cations 104 of the sixth composition 410 can be quaternary ammonium cations. Further, the one or more hydrophobic functional groups 106 can comprise one or more aromatic rings bonded to one or more of the cations 104 (e.g., one or more quaternary ammonium cations). Moreover, the sixth ionene composition 410 can comprise one or more hydrophilic functional groups. The one or more hydrophilic functional groups can comprise one or more ether groups. Also, the one or more hydrophilic functional groups can be bonded to the one or more hydrophobic functional groups 106. In addition, the one or more hydrophilic functional groups can comprise additional cations 104 (e.g., quaternary ammonium cations).

The seventh ionene composition 412 (e.g., comprising an ionene unit 100 that can be characterized by the first chemical formula 200) can comprise a degradable molecular backbone 102 having a plurality of terephthalamide structures. The one or more cations 104 of the seventh composition 412 can be quaternary ammonium cations. Further, the one or more hydrophobic functional groups 106 can comprise one or more aromatic rings, and can be bonded to one or more of the cations 104 (e.g., one or more quaternary ammonium cations). Moreover, the seventh ionene composition 412 can comprise one or more hydrophilic functional groups. The one or more hydrophilic functional groups can be: derived from a block polymer, water-soluble, and/or bioinert. The one or more hydrophilic functional groups can be bonded to one or more cations 104 (e.g., quaternary ammonium cations). Also, the one or more hydrophilic functional groups can comprise one or more ether groups.

The eighth ionene composition 414 (e.g., comprising an ionene unit 100 in accordance with FIG. 1A) can comprise a molecular backbone 102 comprising one or more ether groups. The one or more cations 104 of the eighth ionene composition 414 can be quaternary ammonium cations. Further, the one or more hydrophobic functional groups 106 can comprise one or more aromatic rings, and can be bonded to one or more cations 104 (e.g., one or more quaternary ammonium cations).

Figure 5:
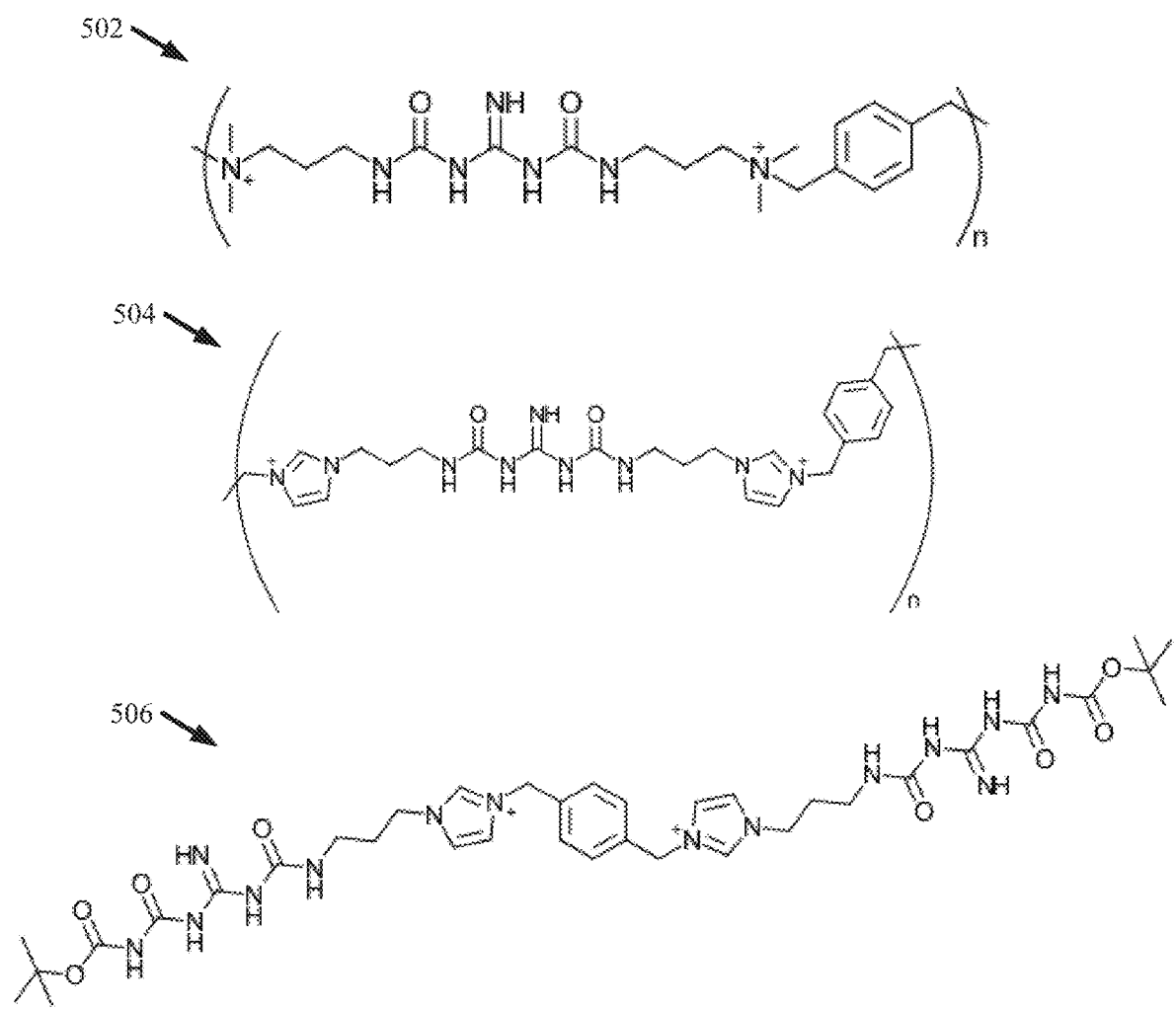
FIG. 5 illustrates a diagram of example, non-limiting ionene compositions that can be utilized in accordance with one or more embodiments described herein.

FIG. 5 illustrates example, non-limiting ionene compositions that can be characterized by the second chemical formula 202 in accordance with one or more embodiments described herein. Repetitive description of like elements employed in other embodiments described herein is omitted for sake of brevity. The "n" shown in FIG. 5 can represent an integer greater than or equal to one and less than or equal to one thousand. The ionene compositions depicted in FIG. 5 can comprise monomers and/or polymers (e.g., homopolymers, alternating copolymers, and/or random copolymers).

The ninth ionene composition 502 (e.g., comprising an ionene unit 100 that can be characterized by the second chemical formula 202) can comprise a degradable molecular backbone 102 having one or more bis(urea)guanidinium structures. The one or more cations 104 of the ninth composition 502 can be quaternary ammonium cations. Further, the one or more hydrophobic functional groups 106 can comprise one or more aromatic rings bonded to one or more of the cations 104 (e.g., one or more quaternary ammonium cations).

The tenth ionene composition 504 (e.g., comprising an ionene unit 100 that can be characterized by the second chemical formula 202) can comprise a degradable molecular backbone 102 having one or more bis(urea)guanidinium structures. The one or more cations 104 of the second composition 402 can be imidazolium cations. Further, the one or more hydrophobic functional groups 106 can comprise one or more aromatic rings bonded to one or more of the cations 104 (e.g., one or more imidazolium cations).

The eleventh ionene composition 506 (e.g., comprising an ionene unit 100 that can be characterized by the second chemical formula 202) can comprise a degradable molecular backbone 102 having a plurality of bis(urea)guanidinium structures. The one or more cations 104 of the second composition 402 can be imidazolium cations. Further, the one or more hydrophobic functional groups 106 can comprise one or more aromatic rings bonded to one or more of the cations 104 (e.g., one or more imidazolium cations). For example, one or more of the hydrophobic functional groups 106 can be bonded to two or more cations 104 (e.g., two or more imidazolium cations). In one or more embodiments, the eleventh ionene composition 506 can be further modified (e.g., functionalized). For example, one or more additional functional groups can replace and/or modify one or more of the tert-butyl groups located at the peripheries of the eleventh ionene composition 506. For instance, Scheme 1, presented below, can depict an exemplary modification to the eleventh ionene composition.

Scheme 1
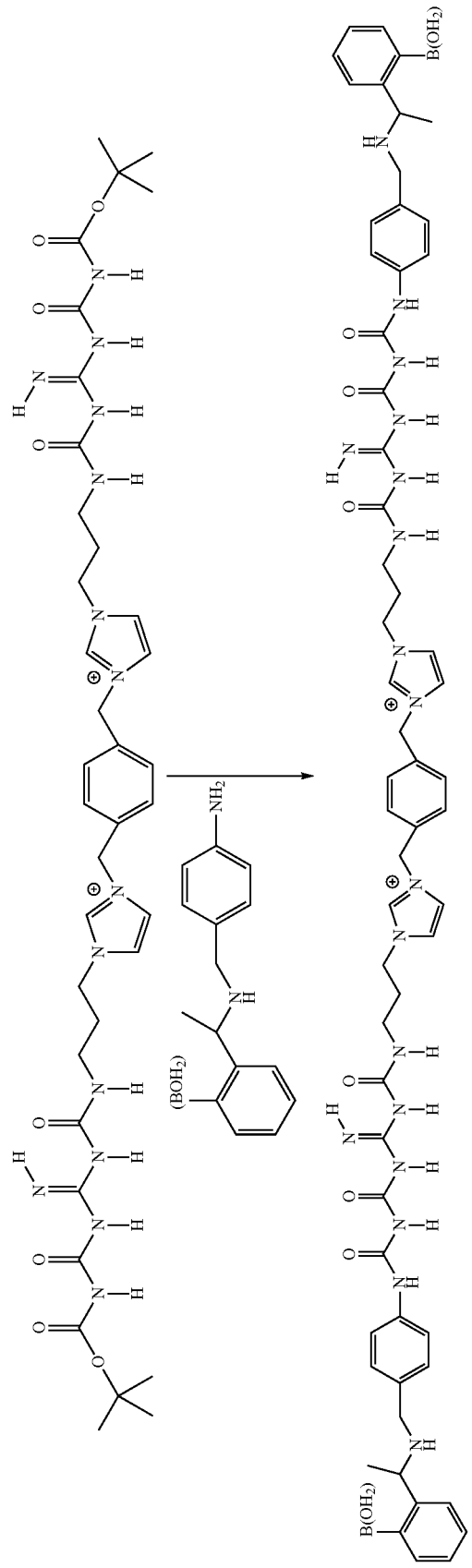

FIG. 6 illustrates a flow diagram of an example, non-limiting method 600 that can facilitate killing a *Mycobacterium tuberculosis* microbe, preventing the growth of a *Mycobacterium tuberculosis* microbe, and/or preventing contamination by a *Mycobacterium tuberculosis* microbe. Repetitive description of like elements employed in other embodiments described herein is omitted for sake of brevity.

At 602, the method 600 can comprise contacting a *Mycobacterium tuberculosis* microbe with one or more chemical compounds. The one or more chemical compounds can comprise one or more ionene units 100 (e.g., characterized by the first chemical formula 200 and/or the second chemical formula 202). The one or more ionene units 100 can comprise one or more cations 104 (e.g., represented by "X" in FIG. 2) distributed along a molecular backbone 102. The one or more cations 104 can comprise nitrogen cations and/or phosphorus cations. Example nitrogen cations can include, but are not limited to: protonated secondary amine cations, protonated tertiary amine cations, quaternary ammonium cations, and/or imidazolium cations. Example phosphorus cations can include, but are not limited to: protonated secondary phosphine cations, protonated tertiary phosphine cations, and/or quaternary phosphonium cations. The molecular backbone 102 can be degradable. Further, the molecular backbone 102 can comprise one or more terephthalamide structures and/or one or more bis(urea) guanidinium structures. The one or more ionene units 100 can have: antimicrobial functionality, supramolecular assembly functionality, and/or carbohydrate mimetic functionality.

At 604, the method 600 can comprise electrostatically disrupting a membrane of the *Mycobacterium tuberculosis* microbe in response to the contacting at 602. The membrane of the *Mycobacterium tuberculosis* microbe can comprise a phospholipid bilayer as described regarding FIG. 1B. Further, the electrostatic disruption at 604 can be facilitated by one or more interactions between the one or more cations 104 of the ionene unit 100 and/or one or more negatively charged membrane molecules 112 that can comprise the membrane of the *Mycobacterium tuberculosis* microbe.

Furthermore, the ionene unit 100 can comprise one or more hydrophobic functional groups 106. The one or more hydrophobic functional groups 106 can be derived from dialkyl halides and can comprise alkyl and/or aryl structures. Additionally, the one or more hydrophobic functional groups 106 can be covalently bonded to the molecular backbone 102 (e.g., via bonding with one or more cations 104). Additionally, the method 600 can further comprise destabilizing the membrane of the *Mycobacterium tuberculosis* microbe through integration of the hydrophobic functional group 106 into the membrane (e.g., as depict at 120 and/or 122 of the lysis process 108).

In one or more embodiments, the ionene unit 100 can further comprise one or more hydrophilic functional groups. The one or more hydrophilic functional groups can: increase degradability of the one or more ionene units 100, impart carbohydrate mimetic functionality to the one or more ionene units 100, and/or increase mobility (e.g., intracellular mobility) of the one or more ionene units 100. For example, the one or more hydrophilic functional groups can be derived from a polyol and have one or more hydroxyl functional groups. In another example, the one or more hydrophilic functional groups can be derived from a block polymer, can be water-soluble, can be bioinert, and/or can comprise one or more ether groups.

In one or more embodiments, the one or more ionene units 100 can supramolecularly assemble with the *Mycobacterium tuberculosis* microbe. For example, one or more bis(urea) guanidinium structures comprising the molecular backbone 102 of the one or more ionene units 100 can facilitate supramolecular assembly of the one or more chemical compounds with the *Mycobacterium tuberculosis* microbe to form a supramolecular assembly.

Thus, the one or more chemical compounds can be monomers (e.g., ionenes) and/or polymers (e.g., polyionenes such as homopolymers, alternating copolymers, and/or random copolymers). The one or more ionene units 100 comprising the one or more compounds utilized in method 600 can be characterized by the first chemical formula 200 and/or the second chemical formula 202. For example, the one or more chemical compounds can comprise any of the ionene compositions described herein (e.g., with regard to FIGS. 3-5). Additionally, the method 600 can facilitate conducting a lysis process 108 regarding the *Mycobacterium tuberculosis* microbe.

FIG. 7 illustrates a flow diagram of an example, non-limiting method 700 that can facilitate killing a *Mycobacterium avium* complex microbe, preventing the growth of a *Mycobacterium avium* complex microbe, and/or preventing contamination by a *Mycobacterium avium* complex microbe. Repetitive description of like elements employed in other embodiments described herein is omitted for sake of brevity.

At 702, the method 700 can comprise contacting a *Mycobacterium avium* complex microbe with one or more chemical compounds. The one or more chemical compounds can comprise one or more ionene units 100 (e.g., characterized by the first chemical formula 200 and/or the second chemical formula 202). The one or more ionene units 100 can comprise one or more cations 104 (e.g., represented by "X" in FIG. 2) distributed along a molecular backbone 102. The one or more cations 104 can comprise nitrogen cations and/or phosphorus cations. Example nitrogen cations can include, but are not limited to: protonated secondary amine cations, protonated tertiary amine cations, quaternary ammonium cations, and/or imidazolium cations. Example phosphorus cations can include, but are not limited to: protonated secondary phosphine cations, protonated tertiary phosphine cations, and/or quaternary phosphonium cations. The molecular backbone 102 can be degradable. Further, the molecular backbone 102 can comprise one or more terephthalamide structures and/or one or more bis(urea) guanidinium structures. The one or more ionene units 100 can have: antimicrobial functionality, supramolecular assembly functionality, and/or carbohydrate mimetic functionality.

At 704, the method 700 can comprise electrostatically disrupting a membrane of the *Mycobacterium avium* complex microbe in response to the contacting at 702. The membrane of the *Mycobacterium avium* complex microbe can comprise a phospholipid bilayer 110 as described regarding FIG. 1B. Further, the electrostatic disruption at 704 can be facilitated by one or more interactions between the one or more cations 104 of the ionene unit 100 and/or one or more negatively charged membrane molecules 112 that can comprise the membrane of the *Mycobacterium avium* complex microbe.

Furthermore, the ionene unit 100 can comprise one or more hydrophobic functional groups 106. The one or more hydrophobic functional groups 106 can be derived from dialkyl halides and can comprise alkyl and/or aryl structures. Additionally, the one or more hydrophobic functional groups 106 can be covalently bonded to the molecular backbone 102 (e.g., via bonding with one or more cations 104). Additionally, the method 700 can further comprise destabilizing the membrane of the *Mycobacterium avium* complex microbe through integration of the hydrophobic functional group 106 into the membrane (e.g., as depict at 120 and/or 122 of the lysis process 108).

In one or more embodiments, the ionene unit 100 can further comprise one or more hydrophilic functional groups. The one or more hydrophilic functional groups can: increase degradability of the one or more ionene units 100, impart carbohydrate mimetic functionality to the one or more ionene units 100, and/or increase mobility (e.g., intracellular mobility) of the one or more ionene units 100. For example, the one or more hydrophilic functional groups can be derived from a polyol and have one or more hydroxyl functional groups. In another example, the one or more hydrophilic functional groups can be derived from a block polymer, can be water-soluble, can be bioinert, and/or can comprise one or more ether groups.

Thus, the one or more chemical compounds can be monomers (e.g., ionenes) and/or polymers (e.g., polyionenes such as homopolymers, alternating copolymers, and/or random copolymers). The one or more ionene units 100 comprising the one or more compounds utilized in method 700 can be characterized by the first chemical formula 200 and/or the second chemical formula 202. For example, the one or more chemical compounds can comprise any of the ionene compositions described herein (e.g., with regard to FIGS. 3-5). Additionally, the method 700 can facilitate conducting a lysis process 108 regarding the *Mycobacterium avium* complex microbe.

FIG. 8 illustrates a flow diagram of an example, non-limiting method 800 that can facilitate killing a pathogen, preventing the growth of a pathogen, and/or preventing contamination by a pathogen. Repetitive description of like elements employed in other embodiments described herein is omitted for sake of brevity. Example pathogens can include, but are not limited to: Gram-negative microbe, a Gram-positive microbe, a fungus, a yeast, a *Mycobacterium tuberculosis* microbe, a *Mycobacterium avium* complex microbe, and/or a *Mycobacterium abscessus* microbe.

At 802, the method 800 can comprise contacting the pathogen with one or more chemical compounds. The one or more chemical compounds can comprise one or more ionene units 100 (e.g., characterized by the second chemical formula 202). The one or more ionene units 100 can comprise one or more cations 104 (e.g., represented by "X" in FIG. 2) distributed along a molecular backbone 102. The one or more cations 104 can comprise nitrogen cations and/or phosphorus cations. Example nitrogen cations can include, but are not limited to: protonated secondary amine cations, protonated tertiary amine cations, quaternary ammonium cations, and/or imidazolium cations. Example phosphorus cations can include, but are not limited to: protonated secondary phosphine cations, protonated tertiary phosphine cations, and/or quaternary phosphonium cations. The molecular backbone 102 can be degradable. Further, the molecular backbone 102 can comprise one or more bis(urea) guanidinium structures. The one or more ionene units 100 can have: antimicrobial functionality and/or supramolecular assembly functionality.

At 804, the method 800 can comprise electrostatically disrupting a membrane of the pathogen in response to the contacting at 802. The membrane of the pathogen can comprise a phospholipid bilayer 110 as described regarding FIG. 1B. Further, the electrostatic disruption at 804 can be facilitated by one or more interactions between the one or more cations 104 of the ionene unit 100 and/or one or more negatively charged membrane molecules 112 that can comprise the membrane of the pathogen.

Additionally, one or more ionene units 100 characterized by the second chemical formula 202 can have supramolecular functionality. For example, the one or more bis(urea) guanidinium structures can facilitate supramolecular assembly of the one or more ionene units 100 with the pathogen to form a supramolecule.

Thus, the one or more chemical compounds can be monomers (e.g., ionenes) and/or polymers (e.g., polyionenes such as homopolymers, alternating copolymers, and/or random copolymers). The one or more ionene units 100 comprising the one or more compounds utilized in method 800 can be characterized by the second chemical formula 202. For example, the one or more chemical compounds can comprise one or more of the ionene compositions described regarding FIG. 5. Additionally, the method 800 can facilitate conducting a lysis process 108 regarding the pathogen.

FIG. 9 illustrates a flow diagram of an example, non-limiting method 900 that can facilitate killing a pathogen, preventing the growth of a pathogen, and/or preventing contamination by a pathogen. Repetitive description of like elements employed in other embodiments described herein is omitted for sake of brevity. Example pathogens can include, but are not limited to: Gram-negative microbe, a Gram-positive microbe, a fungus, a yeast, a *Mycobacterium tuberculosis* microbe, a *Mycobacterium avium* complex microbe, and/or a *Mycobacterium abscessus* microbe.

At 902, the method 900 can comprise contacting the pathogen with one or more chemical compounds. The one or more chemical compounds can comprise one or more ionene units 100 (e.g., characterized by the first chemical formula 200). The one or more ionene units 100 can comprise one or more cations 104 (e.g., represented by "X" in FIG. 2) distributed along a molecular backbone 102. The one or more cations 104 can comprise nitrogen cations and/or phosphorus cations. Example nitrogen cations can include, but are not limited to: protonated secondary amine cations, protonated tertiary amine cations, quaternary ammonium cations, and/or imidazolium cations. Example phosphorus cations can include, but are not limited to: protonated secondary phosphine cations, protonated tertiary phosphine cations, and/or quaternary phosphonium cations. The molecular backbone 102 can be degradable. Further, the molecular backbone 102 can comprise one or more terephthalamide structures. The one or more ionene units 100 can have: antimicrobial functionality and/or carbohydrate mimetic functionality.

At 904, the method 900 can comprise electrostatically disrupting a membrane of the pathogen in response to the contacting at 902. The membrane of the pathogen can comprise a phospholipid bilayer as described regarding FIG. 1B. Further, the electrostatic disruption at 904 can be facilitated by one or more interactions between the one or more cations 104 of the ionene unit 100 and/or one or more negatively charged membrane molecules 112 that can comprise the membrane of the pathogen.

Furthermore, the ionene unit 100 can comprise one or more hydrophobic functional groups 106. The one or more hydrophobic functional groups 106 can be derived from dialkyl halides and can comprise alkyl and/or aryl structures. Additionally, the one or more hydrophobic functional groups 106 can be covalently bonded to the molecular backbone 102 (e.g., via bonding with one or more cations 104). Additionally, the method 900 can further comprise destabilizing the membrane of the pathogen through integration of the hydrophobic functional group 106 into the membrane (e.g., as depict at 120 and/or 122 of the lysis process 108).

In one or more embodiments, the ionene unit 100 can further comprise one or more hydrophilic functional groups. The one or more hydrophilic functional groups can: increase degradability of the one or more ionene units 100, impart carbohydrate mimetic functionality to the one or more ionene units 100, and/or increase mobility (e.g., intracellular mobility) of the one or more ionene units 100. For example, the one or more hydrophilic functional groups can be derived from a polyol and have one or more hydroxyl functional groups. In another example, the one or more hydrophilic functional groups can be derived from a block polymer, can be water-soluble, can be bioinert, and/or can comprise one or more ether groups.

Thus, the one or more chemical compounds can be monomers (e.g., ionenes) and/or polymers (e.g., polyionenes such as homopolymers, alternating copolymers, and/or random copolymers). The one or more ionene units 100 comprising the one or more compounds utilized in method 900 can be characterized by the first chemical formula 200. For example, the one or more chemical compounds can comprise any of the ionene compositions described regarding FIGS. 3-4. Additionally, the method 900 can facilitate conducting a lysis process 108 regarding the pathogen.

FIG. 10 illustrates a flow diagram of an example, non-limiting method 1000 that can facilitate killing a pathogen, preventing the growth of a pathogen, and/or preventing contamination by a pathogen. Repetitive description of like elements employed in other embodiments described herein is omitted for sake of brevity. Example pathogens can include, but are not limited to: Gram-negative microbe, a Gram-positive microbe, a fungus, a yeast, a *Mycobacterium tuberculosis* microbe, a *Mycobacterium avium* complex microbe, and/or a *Mycobacterium abscessus* microbe.

At 1002, the method 1000 can comprise targeting a pathogen with one or more chemical compounds through electrostatic interaction between the one or more chemical compounds and a membrane of the pathogen. For example, the targeting at 1002 can be facilitated by one or more interactions between the one or more cations 104 of the chemical compound and/or one or more negatively charged membrane molecules 112 that can comprise the membrane of the pathogen.

The one or more chemical compounds can comprise one or more ionene units 100 (e.g., characterized by the first chemical formula 200 and/or the second chemical formula 202). The one or more ionene units 100 can comprise the one or more cations 104 (e.g., represented by "X" in FIG. 2) distributed along a molecular backbone 102. The one or more cations 104 can comprise nitrogen cations and/or phosphorus cations. Example nitrogen cations can include, but are not limited to: protonated secondary amine cations, protonated tertiary amine cations, quaternary ammonium cations, and/or imidazolium cations. Example phosphorus cations can include, but are not limited to: protonated secondary phosphine cations, protonated tertiary phosphine cations, and/or quaternary phosphonium cations. The molecular backbone 102 can be degradable. Further, the molecular backbone 102 can comprise one or more terephthalamide structures and/or one or more bis(urea)guanidinium structures. The one or more ionene units 100 can have: antimicrobial functionality, supramolecular assembly functionality, and/or carbohydrate mimetic functionality.

Furthermore, the ionene unit 100 can comprise one or more hydrophobic functional groups 106. The one or more hydrophobic functional groups 106 can be derived from dialkyl halides and can comprise alkyl and/or aryl structures. Additionally, the one or more hydrophobic functional groups 106 can be covalently bonded to the molecular backbone 102 (e.g., via bonding with one or more cations 104).

At 1004, the method 1000 can further comprise destabilizing the membrane of the pathogen through integration of the one or more hydrophobic functional groups 106 into the membrane of the pathogen. For example, the one or more hydrophobic functional groups 106 can integrate into a hydrophobic region of the membrane as depicted at 120 and/or 122 of the lysis process 108. Integration of the one or more hydrophobic functional groups 106 can compromise the integrity of the pathogen's membrane, thereby facilitating the lysis process 108.

In one or more embodiments, the ionene unit 100 can further comprise one or more hydrophilic functional groups. The one or more hydrophilic functional groups can: increase degradability of the one or more ionene units 100, impart carbohydrate mimetic functionality to the one or more ionene units 100, and/or increase mobility (e.g., intracellular mobility) of the one or more ionene units 100. For example, the one or more hydrophilic functional groups can be derived from a polyol and have one or more hydroxyl functional groups. In another example, the one or more hydrophilic functional groups can be derived from a block polymer, can be water-soluble, can be bioinert, and/or can comprise one or more ether groups.

In one or more embodiments, the one or more ionene units 100 can supramolecularly assemble with the pathogen. For example, one or more bis(urea)guanidinium structures comprising the molecular backbone 102 of the one or more ionene units 100 can facilitate supramolecular assembly of the one or more chemical compounds with the pathogen to form a supramolecular assembly.

Thus, the one or more chemical compounds can be monomers (e.g., ionenes) and/or polymers (e.g., polyionenes such as homopolymers, alternating copolymers, and/or random copolymers). The one or more ionene units 100 comprising the one or more compounds utilized in method 1000 can be characterized by the first chemical formula 200 and/or the second chemical formula 202. For example, the one or more chemical compounds can comprise any of the ionene compositions described herein (e.g., with regard to FIGS. 3-5). Additionally, the method 1000 can facilitate conducting a lysis process 108 regarding the *Mycobacterium tuberculosis* microbe.

Figure 11:
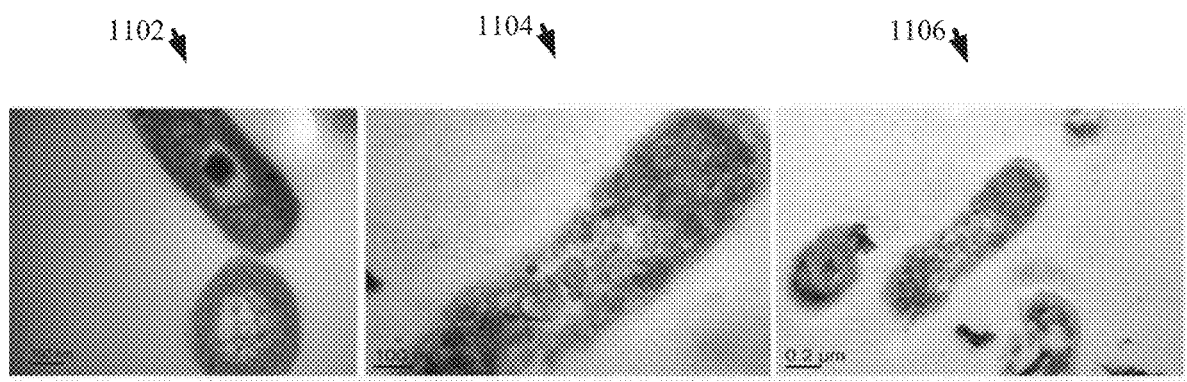
FIG. 11 illustrates three micrographs of an example, non-limiting lysis process in accordance with one or more embodiments described herein.

FIG. 11 illustrates three micrographs of an example, non-limiting lysis process 108 of a *Mycobacterium tuberculosis* 3360 (Mtb 3360) microbe, which is a clinical strain of *Mycobacterium tuberculosis*, in accordance with one or more embodiments described herein. Repetitive description of like elements employed in other embodiments described herein is omitted for sake of brevity. FIG. 11 can depict transmission electron microscopy (TEM) micrographs of a Mtb 3360 microbe undergoing a lysis process 108 facilitated by the fifth ionene composition 408 at a concentration of 32 micrograms per milliliter (µg/mL). The first micrograph 1102 can depict the Mtb 3360 microbe before being contacted with the fifth ionene composition 408. The second micrograph 1104 and/or the third micrograph 1106 can depict the Mtb 3360 microbe after being contacted with the fifth ionene composition 408 for 24 hours.

FIG. 12A illustrates a diagram of an example, non-limiting chart 1200 that can depict the antimicrobial efficacy of one or more ionene compositions in accordance with one or more embodiments described herein. Repetitive description of like elements employed in other embodiments described herein is omitted for sake of brevity. To demonstrate the antimicrobial effects of the ionene compositions (e.g., that can be characterized by first chemical formula 200 and/or second chemical formula 202 and exemplified in FIGS. 3-5) and methods (e.g., methods 600, 700, 800, 900, and/or 1000) described herein a plurality of polyionene compositions were evaluated against a broad spectrum of pathogens.

The first column 1202 of chart 1200 can depict the ionene composition subject to evaluation. The second column 1204 of chart 1200 can depict the minimum inhibitory concentration (MIC) in μg/mL of the subject ionene composition regarding *Staphylococcus aureus* ("SA"). The third column 1206 of chart 1200 can depict the MIC in μg/mL of the subject ionene composition regarding *Escherichia coli* ("EC"). The fourth column 1208 of chart 1200 can depict the MIC in μg/mL of the subject ionene composition regarding *Pseudomonas aeruginosa* ("PA"). The fifth column 1210 of chart 1200 can depict the MIC in μg/mL of the subject ionene composition regarding *Candida albicans* ("CA"). The sixth column 1212 of chart 1200 can depict the MIC in μg/mL of the subject ionene composition regarding Mtb 3360. The seventh column 1214 of chart 1200 can depict the MIC in μg/mL of the subject ionene composition regarding Mtb 3361, which is another clinical strain of *Mycobacterium tuberculosis*.

FIG. 12B illustrates a diagram of an example, non-limiting chart 1216 that can depict the antimicrobial efficacy of one or more ionene compositions in accordance with one or more embodiments described herein. Repetitive description of like elements employed in other embodiments described herein is omitted for sake of brevity. To demonstrate the antimicrobial effects of the ionene compositions (e.g., that can be characterized by first chemical formula 200 and/or second chemical formula 202 and exemplified in FIGS. 3-5) and methods (e.g., methods 600, 700, 800, 900, and/or 1000) described herein a plurality of polyionene compositions were evaluated against *Mycobacterium avium* complex and/or *Mycobacterium abscessus* 4064, which is a clinical strain of *Mycobacterium abscessus*.

The left column 1218 of chart 1216 can depict the ionene composition subject to evaluation. The middle column 1220 of chart 1216 can depict the MIC in μg/mL of the subject ionene composition regarding *Mycobacterium avium* complex. The right column 1222 of chart 1200 can depict the MIC in μg/mL of the subject ionene composition regarding *Mycobacterium abscessus* 4064.

The various structures (e.g., described regarding FIG. 2), compositions (e.g., described regarding FIGS. 3-5 and/or 11-12), and/or methods (e.g., described regarding FIGS. 6-10) described herein can be incorporated into a variety of applications. For example, said applications can include cleaning, sanitizing, disinfecting, and/or otherwise treating various articles such as, but not limited to: food packaging, medical devices, floor surfaces, furniture surfaces, wound care instruments (e.g., bandages and/or gauss), building surfaces, plants (e.g., agricultural crops), ground surfaces, farming equipment, beds, sheets, clothes, blankets, shoes, doors, door frames, walls, ceilings, mattresses, light fixtures, facets, switches, sinks, grab rails, remote controls, vanities, computer equipment, carts, trolleys, hampers, bins, a combination thereof, and/or the like. In another example, said applications can include pharmaceuticals, pharmaceutical salts, hygiene products (e.g., soaps and/or shampoos), air filters, masks, air purifiers, and/or the like. In a further example, said applications can include agricultural sprays and/or aqueous solutions that can facilitate processing crops for consumption.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

What has been described above include mere examples of systems, compositions, and methods. It is, of course, not possible to describe every conceivable combination of reagents, products, solvents, and/or articles for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for inhibiting *Mycobacterium tuberculosis*, comprising:

contacting a *Mycobacterium tuberculosis* microbe with a chemical compound, the chemical compound comprising an ionene unit, and the ionene unit comprising a cation distributed along a molecular backbone, wherein the ionene unit has antimicrobial functionality, wherein the molecular backbone is degradable, and wherein the chemical compound is characterized by the following structure:

$$\left( -X-L-\underset{H}{N}-\underset{O}{\overset{\displaystyle \phantom{O}}{\underset{\phantom{O}}{C}}}-\!\!\!\!\phantom{}-\!\!\!\!\phantom{}-\underset{O}{\overset{\displaystyle \phantom{O}}{\underset{\phantom{O}}{C}}}-\underset{H}{N}-L-X- \right)_n,$$

wherein X is the cation, wherein R is a hydrophobic functional group, wherein n is an integer greater than or equal to two and less than or equal to one thousand, and wherein L is a linkage group selected from the group consisting of an ester group and a carbonyl group; and electrostatically disrupting a membrane of the *Mycobacterium tuberculosis* microbe in response to the contacting.

2. The method of claim 1, wherein the method further comprises:
destabilizing the membrane through integration of the hydrophobic functional group into the membrane.

3. The method of claim 1, wherein the cation is a nitrogen cation selected from the group comprising a protonated secondary amine cation, a protonated tertiary amine cation, a quaternary ammonium cation and an imidazolium cation.

4. The method of claim 3, wherein the method further comprises:
destabilizing the membrane through integration of the hydrophobic functional group into the membrane.

5. A method for inhibiting *Mycobacterium tuberculosis*, comprising:
contacting a *Mycobacterium tuberculosis* microbe with a chemical compound, the chemical compound comprising an ionene unit, and the ionene unit comprising a cation distributed along a molecular backbone, wherein the ionene unit has antimicrobial functionality, wherein the molecular backbone is degradable, and wherein the chemical compound is characterized by the following structure:

$$\left( -X-L-\underset{H}{N}-\underset{H}{\overset{O}{\overset{\|}{C}}}-\underset{H}{N}-\underset{H}{\overset{NH}{\overset{\|}{C}}}-\underset{H}{N}-\underset{H}{\overset{O}{\overset{\|}{C}}}-\underset{H}{N}-L-X-R \right)_n,$$

wherein X is the cation, wherein R is a hydrophobic functional group, wherein n is an integer greater than or equal to two and less than or equal to one thousand, and wherein L is a linkage group selected from the group consisting of: an alkyl group, aryl group, an alkenyl group, an aldehyde group, an ester group, a carboxyl group, and a carbonyl group; and electrostatically disrupting a membrane of the *Mycobacterium tuberculosis* microbe in response to the contacting.

6. The method of claim 5, wherein the cation is a nitrogen cation selected from the group comprising a protonated secondary amine cation, a protonated tertiary amine cation, a quaternary ammonium cation and an imidazolium cation.

7. The method of claim 6, wherein the method further comprises:
destabilizing the membrane through integration of the hydrophobic functional group into the membrane.

8. The method of claim 5, wherein the ionene unit has a chemical structure selected from the group consisting of:

9. A method for inhibiting *Mycobacterium tuberculosis*, comprising:
contacting a *Mycobacterium tuberculosis* microbe with a chemical compound, the chemical compound comprising an ionene unit, and the ionene unit comprising a cation distributed along a molecular backbone, wherein the ionene unit has antimicrobial functionality, wherein the molecular backbone is degradable; and electrostatically disrupting a membrane of the *Mycobacterium tuberculosis* microbe in response to the contacting, wherein the ionene unit has a chemical structure selected from the group consisting of:

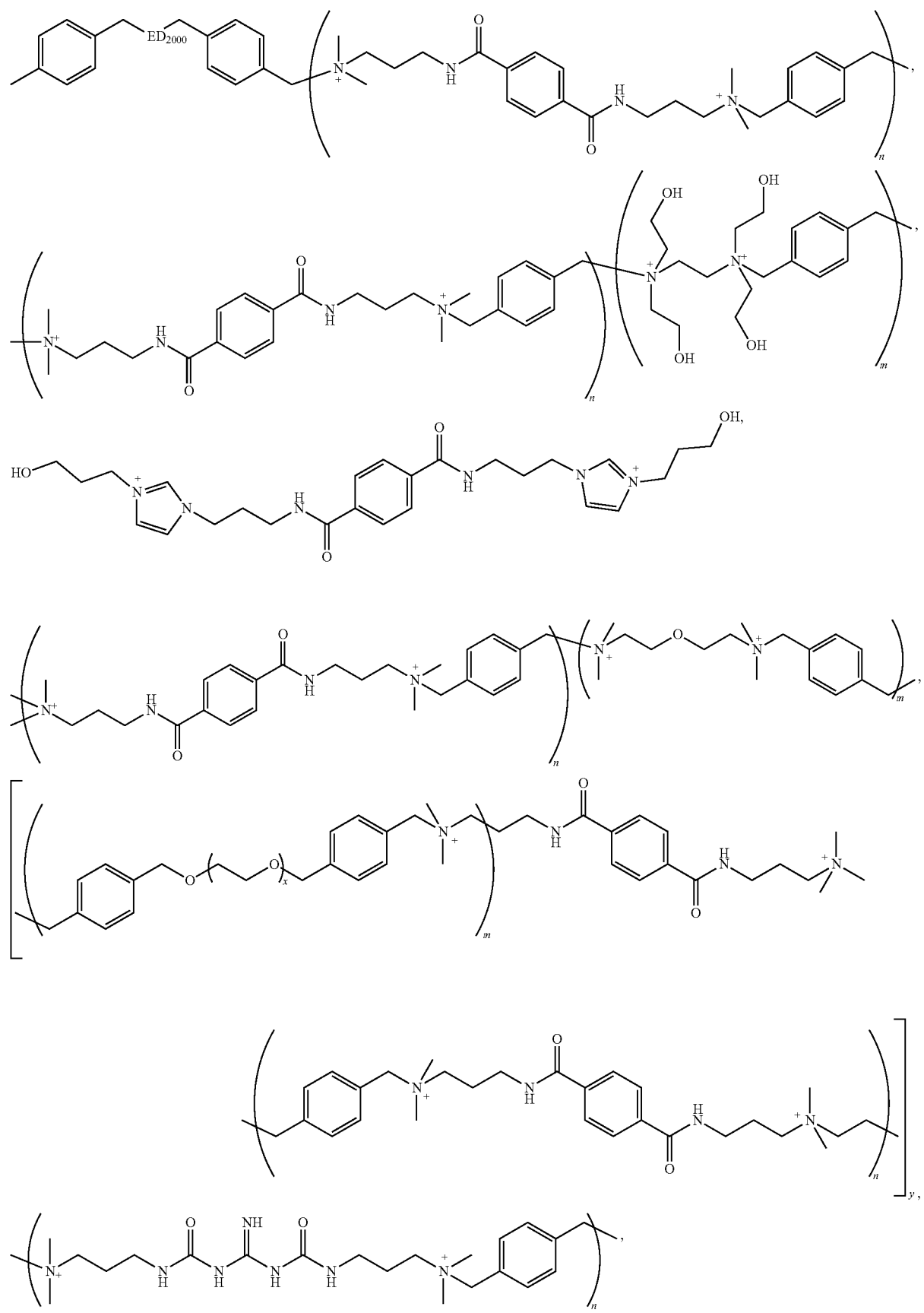

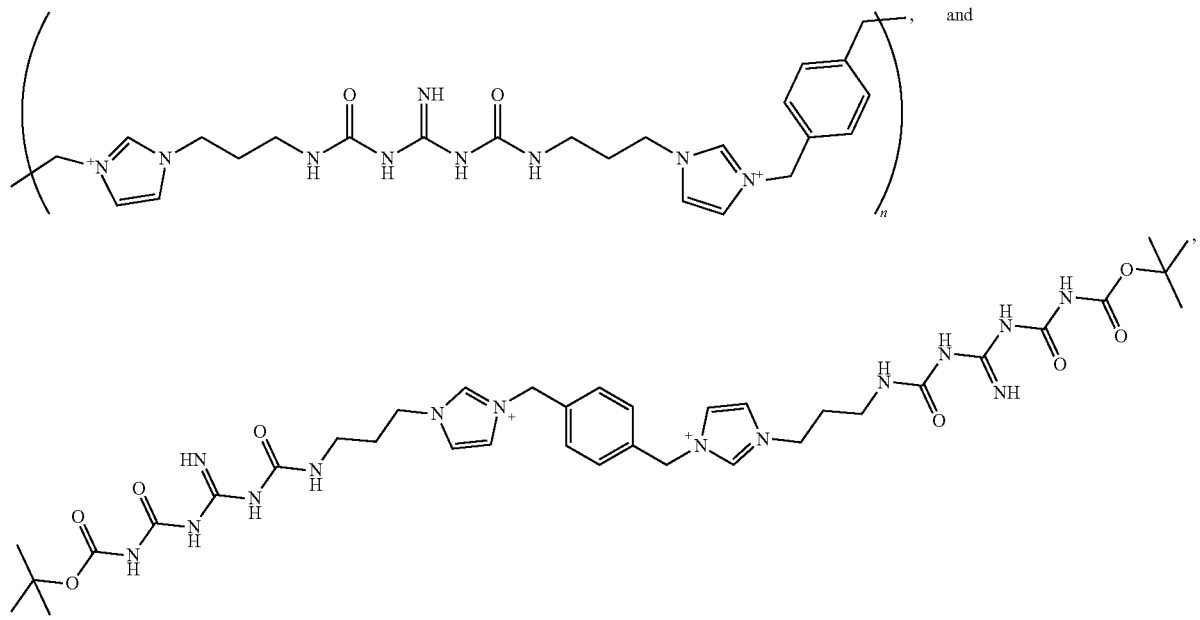

wherein n is a first integer greater than or equal to one and less than or equal to one thousand, wherein m is a second integer greater than or equal to one and less than or equal to one thousand, wherein y is a third integer greater than or equal to one and less than or equal to one thousand, wherein x is a fourth integer greater than or equal to one and less than or equal to one thousand, and wherein $ED_{2000}$ is a poly(propylene glycol)-block-poly(ethylene glycol)-block-poly(propylene glycol) bis(2-aminopropyl ether) structure having a molecular weight greater than or equal to 1900 grams per mole and less than or equal to 2200 grams per mole.

* * * * *